US011845206B2

(12) United States Patent
Raja et al.

(10) Patent No.: US 11,845,206 B2
(45) Date of Patent: Dec. 19, 2023

(54) NASAL IMPRESSION ASSEMBLY AND METHOD OF MEASURING/IMPRINTING THE NASAL IMPRESSION

(71) Applicants: CMH Lahore Medical College & IOD, Lahore (PK); Hina Zafar Raja, Lahore (PK); Muhammad Nasir Saleem, Lahore (PK)

(72) Inventors: Hina Zafar Raja, Lahore (PK); Muhammad Nasir Saleem, Lahore (PK)

(*) Notice: Subject to any disclaimer, the term of this patent is extended or adjusted under 35 U.S.C. 154(b) by 51 days.

(21) Appl. No.: 17/677,476

(22) Filed: Feb. 22, 2022

(65) Prior Publication Data

US 2023/0008837 A1   Jan. 12, 2023

(30) Foreign Application Priority Data

Jul. 6, 2021   (PK) ..................... 506/2021

(51) Int. Cl.
*B29C 45/03*   (2006.01)
*B29C 45/17*   (2006.01)
(Continued)

(52) U.S. Cl.
CPC ........ *B29C 45/036* (2013.01); *B29C 45/1773* (2013.01); *B29C 45/20* (2013.01); *A61F 5/08* (2013.01); *B29L 2031/40* (2013.01)

(58) Field of Classification Search
CPC ... B29C 45/036; B29C 45/1773; B29C 45/20; A61F 5/08
See application file for complete search history.

(56) References Cited

U.S. PATENT DOCUMENTS 704,518 A * 7/1901 Collver
4,243,362 A * 1/1981 Rees ................... B29C 45/1628
425/134

(Continued)

FOREIGN PATENT DOCUMENTS

CN   107696402 A * 2/2018 ............. B29B 13/10
CN   108943578 A * 12/2018
EP   1504871 A2 * 2/2005 ........... B29C 31/044

OTHER PUBLICATIONS

Lipton J. et. al. Fab@Home Model 2: Towards Ubiquitous Personal Fabrication Devices, Cornell University (2009)https://repositories.lib.utexas.edu/bitstream/handle/2152/88149/2009-08-Lipton.pdf?sequence=2&isAllowed=y (Year: 2009).*

(Continued)

*Primary Examiner* — Matthew J Daniels
*Assistant Examiner* — Wayne K. Swier
(74) *Attorney, Agent, or Firm* — Fitch, Even, Tabin & Flannery, LLP (57) ABSTRACT

A nasal impression assembly for use in prosthodontics and otolaryngology, wherein the assembly includes detachable components specifically designed for recording precise nasal impressions. The detachable components may include plurality of nasal cones, a pair of injection syringes, and an extra nasal mesh splint, assembled on a horizontal bar. Further a method is provided for measuring/imprinting the impression, by using the assembly, wherein an impression material is brought in contact with extra-nasal and/or intra-nasal structure to imprint its size and/or shape.

17 Claims, 5 Drawing Sheets

(51) Int. Cl.
    *B29C 45/20*     (2006.01)
    *B29L 31/40*     (2006.01)
    *A61F 5/08*      (2006.01)

(56) References Cited

U.S. PATENT DOCUMENTS

2007/0128305 A1* 6/2007 Parmenter ........... B29C 45/2606
                                                    425/589
2015/0005806 A1* 1/2015 Mejia .................. B29C 39/10
                                                    264/222

OTHER PUBLICATIONS

Rueschhoff, L. et. al. Near-net shaping of silicon nitride via aqueous room-temperature injection molding and pressureless sintering, Ceramics International (2017) School of Material Engineering, Purdue University from https://pdf.sciencedirectassets.com/ (Year: 2017).*
Machine translation CN108943578A (Year: 2018).*
Machine translation CN107696402A (Year: 2018).*
Metzinger SE. Diagnosing and treating nasal septal perforations. Aesthet Surg J. 2005;25(5):524-9.
Passali D, Spinosi MC, Salerni L, Cassano M, Rodriguez H, Passali FM, et al. Surgical treatment of nasal septal perforations: SIR (Italian Society of Rhinology) experts opinion. Acta Otorrinolaringol Esp. 2017;68(4):191-6.
Hussein S. Zaki, DDS, MS, a and Eugene N. Myers, MD; Prosthetic management of large nasal septal defects. The Journal of Prosthetic Dentistry, Mar. 1997, vol. 77 No. 3, 335-338.
Vincent K. L. Yeow, M.B.B.S.(Sing.), F.R.C.S.(Ed.), F.R.C.S. (Glasg.), Philip K. T. Chen, M.D., Yu-Ray Chen, M.D., and Samuel M. Noordoff, M.D., F.A.C.S.; The Use of Nasal Splints in the Primary Management of Unilateral Cleft Nasal Deformity; Plastic and Reconstructive Surgery, Apr. 1999, 1347-1354.
Blind A, Hulterström A, Berggren D. Treatment of nasal septal perforations with a custom-made prosthesis. European Archives of Oto-Rhino-Laryngology. 2009;266(1):65-9.
Hasan Farook T, Jamayet N. A review of prostheses fabricated for rehabilitation of nasal septal defect using digital workflow. Otorinolaringologia. 2020;70.
Goh AY, Hussain SS. Different surgical treatments for nasal septal perforation and their outcomes. J Laryngol Otol. 2007;121(5):419-26.
Goyal MK, Goyal S. Prosthetic rehabilitation of large nasal septal defect with an intranasal stent: a clinical report. Indian J Dent Res. 2011;22(5):719-22.
Somohano Marquez T. Custom Nasal Septum Prosthesis Fabricated from a 3D-Printed Working Model: A Clinical Report. Journal of Prosthodontics. 2019;28(5):493-6.
Sashi Purna CR, Annapurna PD, Ahmed SB, Vurla S, Nalla S, Abhishek SM. Two-piece nasal septum prosthesis for a large nasal septum perforation: a clinical report. J Prosthodont. 2013;22(2):143-7.
Nagaraj E, Shetty M, Krishna PD. Definitive magnetic nasal prosthesis for partial nasal defect. Indian Journal of Dental Research. 2011;22(4):597.
M. Mullace, E. Gorini, M. Sbrocca, L. Artesi, N. Mevio. Management of nasal septal perforation using silicone nasal septal button. Acta Otorhinolaryngol Ital 26, 216-218, 2006.
Teny Fernandez, Harshakumar Karunakaran, Sheela Virginia Rodrigues; Prosthetic Management of a Nasal Septal Defect using a Custom Made Unilateral Intranasal Stent: A Case Report; Journal of Clinical and Diagnostic Research. Aug. 2016, vol. 10(8): ZD33-ZD34.
A. Hussain, F.R.C.S., P. Murthy, F.R.C.S .; Modified tragal cartilage—temporoparietal and deep temporal fascia sandwich graft technique for repair of nasal septal perforations. The Journal of Laryngology and Otology May 1997, vol. III, pp. 435-437.
James R. Moergeli, Jr., D.D.S.; An improved obturator for a defect of the nasal septum. The Journal of Prosthetic Dentistry, Apr. 1982, vol. 47, No. 4, 419-421.
Richard R. Seals, Jr., D.D.S., M.Ed., MS., Lily Garcia Bohnenkamp, D.D.S., M.S., and Stephen M. Parel, D.D.S.; Intranasal prostheses, splints, and stents; The Journal of Prosthetic Dentistry, Nov. 1988 vol. 60 No. 5, 595-601.

* cited by examiner

NASAL IMPRESSION ASSEMBLY AND METHOD OF MEASURING/IMPRINTING THE NASAL IMPRESSION

CROSS-REFERENCE TO RELATED APPLICATION

This application claims priority from Pakistan Patent Application Number PK 506/2021, filed Jul. 6, 2021, which is hereby incorporated herein by reference in its entirety for all purposes.

FIELD OF INVENTION

The present invention relates generally to a device for measuring/imprinting the impression of an object and particularly for recording precise measurement of extra-nasal and intra-nasal impression in the field of prosthodontics as well as otolaryngology.

DESCRIPTION OF THE PRIOR ARTS

Intra-nasal impressions are required to construct intra-nasal prosthesis in the form of intra-nasal stents, splints or obturators. Impressions are constructed to restore the congenital, traumatic or acquired defects as well as insufficiencies. The construction of an obturator for nasal septal perforation involves impression of the defect area. Although a number of impression techniques are proposed, however, precise manual nasal impression are still challenging for prosthodontists. Majority of failures in retention of prosthesis are due to inadequate records of the defect area.

Techniques for impression have been disclosed in several prior arts. One of it involves outlining of the defected area of the nose with a blotting paper and the remaining dry portion is used to cut out a piece of Silastic, which is 4-5 mm in thickness, as a defect obturator.

Another involves a piece of paper placed on one chamber and perforation is outlined with a cotton carrier dipped in thimerosal (a mercury based preservative), cotton swab or a tongue blade with a mold material carried into the nose for record of perforation.

Yet another technique discloses injection of a silicone material into the nose with a cotton tip applicator, the impression surface of freshly mixed silicone is dampened, prior to its insertion into nasal cavity. In the contralateral nostril, a disposable syringe is used to inject silicone to flow through the defect. A spatula is used to spread the material around the defect area. In this technique, impression of only one nasal cavity is recorded at a time.

One more prior invented technique uses hollow intra-nasal inserts made in modelling plastic, to make intra-nasal impression with the help of impression waxes. Each impression covers approximately 2 cm of intra-nasal area. This involves, softening of impression compound and moulding it in the form of cylinder to record intra-nasal impression. The impression is then processed with clear polymethyl methacrylate. It is kept hollow for free passage of air through the nose. After model pouring, stents with handles are made in auto polymerizing acrylic resin. The stents conform to medial two thirds of the nose of each nostril. Each stent is then utilized as a special tray in respective nostril. Low fusing compound is carried into each nasal cavity individually while utilizing tongue blade to adapt impression material initially and then on contralateral stent to adapt the later one. Impression material is retained with tray adhesive. Extra-nasal impression is taken with alginate. Intra-nasal impression and extra-nasal impressions are joined together at nares and removed collectively. Modelling wax closes the gaps between both impressions. The stability of intra-nasal impressions is achieved with rigid extra-nasal impression. Intra-nasal casts are used to make customized silicone buttons. Intra-nasal buttons are inserted under general or local anesthesia.

Historically, Alginate has also been used to record intra-nasal impression, since it is a tissue friendly material, wherein, tamponades can be used to block out deeper parts of nasal cavity. Alginate mass is carried with a spatula to fill each naris individually. Once set, it is removed and model is poured in multiple steps.

Additionally, a hollow stainless steel ball pen has also been used to carry addition silicone putty with light body wash to record individual impression of a unilateral nasal cavity.

Furthermore, computerized tomographic scans have also been used to construct customized prosthesis. High resolution CT scan of nose and sinuses are done at a slice thickness ranging from 0.32 to 1 mm. A virtual model is created from the segmented data. This model is printed for prosthesis fabrication. Although, nasal prosthesis fabricated with computerized scanning showed better retention rates than manual prosthesis but this facility is not readily available in all parts of world and tends to be expensive. Further research in larger sample size is still needed to prove the significant impact of 3-D scanning in all kinds of nasal restorations.

Although a number of impression techniques are proposed however precise manual nasal impression are still challenging for prosthodontists. Majority of failures in retention of prosthesis are due to inadequate records of the defect area. In addition, it is difficult to make intra nasal impressions of both nostrils collectively. The splinting of intra nasal and extra nasal impressions is also unpredictable due to lack of specific armamentarium.

The present invention allows convenient use of materials for impression making (Alginate) and Model making (Plaster of Paris), which reduces the total cost of the procedure as compared to the expensive equipment for digital work flow (Digital scanning and model pouring).

SUMMARY OF THE INVENTION

The present invention relates to a nasal impression assembly for imprinting/measuring precise measurement of extra-nasal and intra-nasal area comprising detachable components for recording impression(s) of both areas individually or consecutively.

The present invention relates to a nasal assembly comprising detachable components including nasal cones for insertion into the nasal cavity for measuring the intranasal impression, injection syringes affixed with the respective cones for introducing the impression material, and an extra-nasal mesh splint for measuring/imprinting the extranasal impression, wherein all the components are assembled on a horizontal bar which is adjustable in accordance with the anatomical variation of each individual's nose.

The present invention also includes imprinting steps by introducing the assembly i.e. nasal cone configured with the injection syringe into the nasal cavity, whereby the impression material is being introduced in the cone through injection syringes until the nasal cavity(ies) is entirely filled. Upon setting of the material, the assembly is pulled out of the nostrils for model making.

According to the present invention, the extra-nasal mesh splint can be additionally affixed with the impression assembly for taking the impression of the exterior surface, wherein the impression material is poured over the nose for imprinting/measuring the shape, structure and/or size.

BRIEF DESCRIPTION OF THE DRAWINGS

An exemplary or preferably embodiment of the present invention is illustrated in the accompanying drawing in which.

DESCRIPTION OF THE INVENTION

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of method and arrangement of parts and components of the invention set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component or part is intended also to include their plurality. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

The parts described as making up the various elements of the invention are intended to be illustrative and not restrictive. Many suitable components, parts that would perform the same or a similar function as the components and parts described herein are intended to be embraced within the scope of the invention. Such other components/parts not described herein include, but are not limited to, components/parts that may be developed after the time of the development of the invention.

In the following description, reference is made to the accompanying drawings where, by way of illustration, specific exemplary embodiments of the present invention are detailed.

Figure 1:
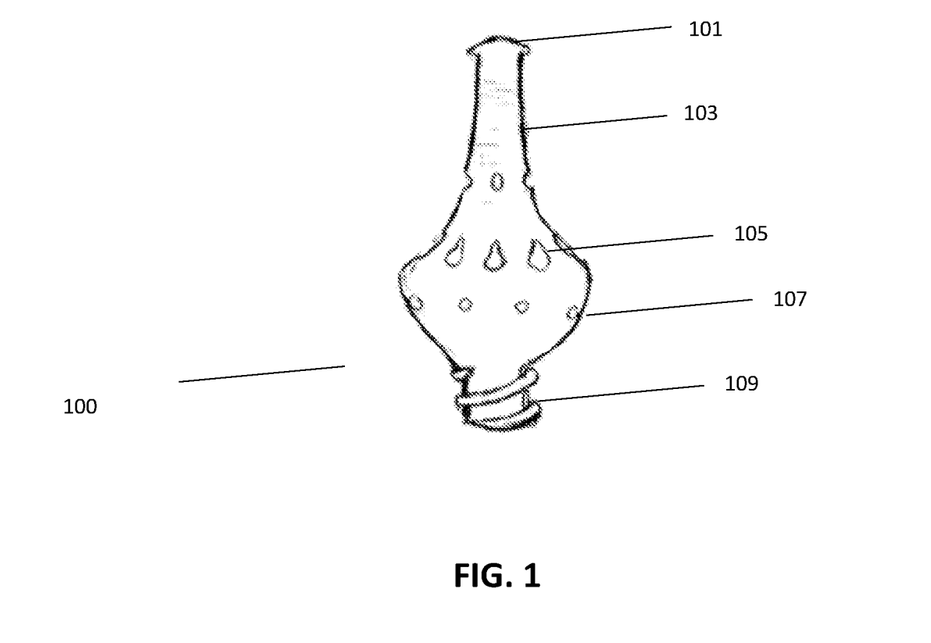
FIG. 1: Illustrates nasal cones of exemplary embodiment of the present invention.

FIG. 1 illustrates a single nasal cone 100 of an exemplary embodiment of the present invention, which is shaped in the form of an elongated flower vase (Sorori shape) having a tip 101 and a base 107. The nasal cones 100 are introduced in the nostrils and are detachably configured with the nasal assembly 500.

According to exemplary embodiment of the present invention, the Sorori shape of the nasal cones conform to the anatomical structure of the nasal cavity(ies), thus allowing more precise impression details of the required area.

In an exemplary embodiment, tip of the cone 101 is mushroom shaped to conform to the mesially directed tilt of the nasal cavity(ies) and for minimum impingement of the fragile nasal mucosa during insertion and removal of the device. The base of the cone 107 is perforated 105 and at the bottom most region, there is a protrusion with screw threads 109 for fixation of cone to the horizontal bar 300.

In accordance to the embodiment of present invention, the nasal cones 100 allow complete flow of material to the entire nasal cavity(ies) as well as the defect area, wherein the mushroomed tip of the cone 101 directs the material towards proximal and supero-inferior walls of the cavity, with lesser chances of material entrapment into the posterior part of nasal cavity. The nasal cones 100 are mesially pre-angulated to an angle of 20° upon fixation to the horizontal bar 300 in order to accommodate the mesial convergence of both nares and avoid the trauma to nasal mucosa of distal walls, during insertion and removal of nasal trays.

Figure 2:
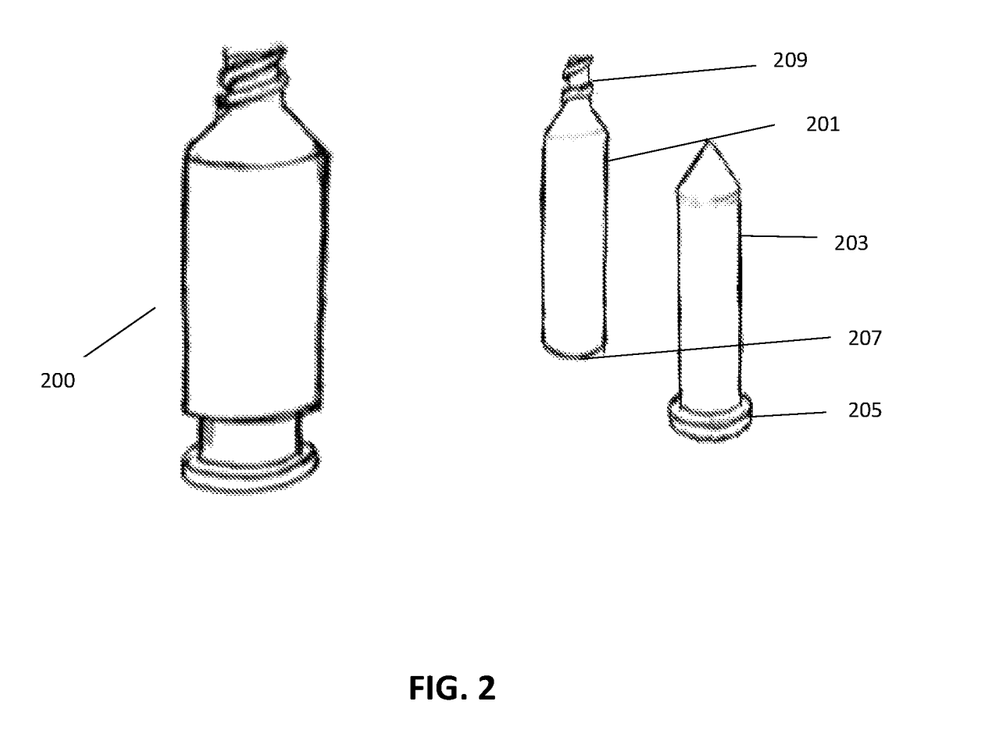
FIG. 2: Illustrates the injection syringe according to exemplary embodiment of the present invention.

FIG. 2 illustrates two detachable injection syringes 200, for each of the respective nostril. The injection syringe is characterized into two parts i.e. Matrix 201 and the Patrix 203. Accordingly, Patrix part 203 is a solid plunger having a push handle 205 at the distal end whereas Matrix 201 is a hollow elongated cylinder with axial cavity 207 at one end and screw threads 209 etched on hub of the syringe for fastening with the screw threads lined inside hole of the horizontal bar 300. According to an exemplary embodiment, the impression material is filled inside the matrix part 201, before presenting/introducing the patrix part 203 through its axial cavity 207.

Figure 3:
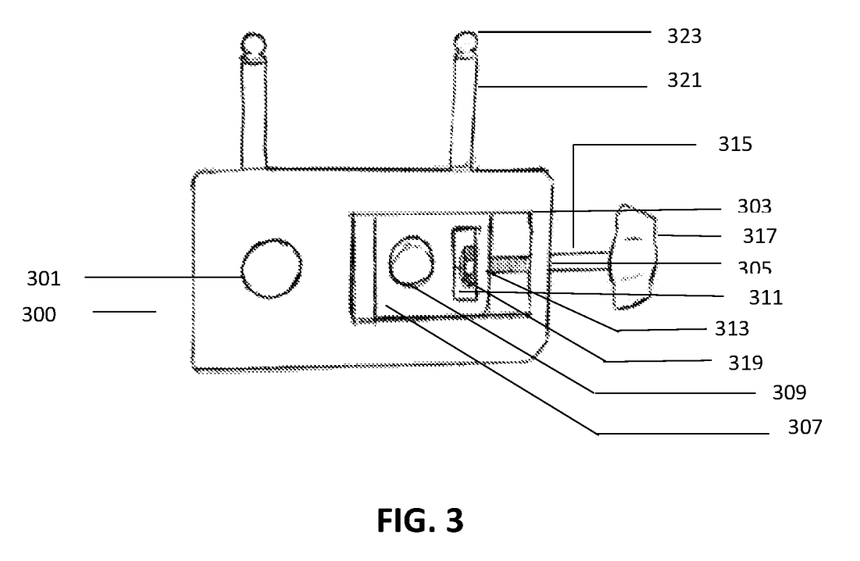
FIG. 3: Illustrates an anterior view of a horizontal bar, according to exemplary embodiment of the present invention.

FIG. 3 illustrates an anterior view of the horizontal bar which is designed for assembling/arranging all detachable components of the assembly. The anterior surface of the horizontal bar 300 may be equally divided into two parts, wherein the left part comprises a circular hole 301 with smooth surface in the surroundings, and wherein the hole is lined internally with screw threads for affixation of the nasal cones 100 anteriorly and injection syringes 200 posteriorly, whereas the right part has a rectangular slot 303 with additional small circular hole 305 in the right lateral edge of the horizontal bar 300, to pass a screw rod 315 therefrom, whereby the small hole 305 may also be lined internally with screw threads.

In the exemplary embodiment, a small slidable block 307 may be designed with the configurations required to slide the said block within and along the walls of the rectangular slot 303 of the horizontal bar 300. In one of the exemplary embodiments, the slidable block 307 may be divided into left and right portion wherein the left portion comprises a circular hole 309, lined internally with screw threads and configured to affix the nasal cone 100 anteriorly and the injection syringe 200 posteriorly whereas the right portion comprises an orifice 311 with an inlet 313 at its lateral right edge. The inlet 313 at the lateral edge of the orifice 311 is coplanar with the small hole 305 in the right lateral edge of the horizontal bar 300. The coplanar arrangement allows the passage of the screw rod 315 coming from the right side of the horizontal bar 300 into the orifice 311 of the slidable block 307, wherein a bolt 319 is affixed at the distal end of the screw rod 315 within the orifice 311, whereas a screw handle 317 is operably attached to the proximal end outside the horizontal bar 300.

In yet another exemplary embodiment of the present invention, the slidable block 307 may comprise a hole 309 lined with screw threads interiorly, to affix the nasal cone 100 and injection syringe 200 in a pre-defined angular manner. The position of said hole 309 in the horizontal bar 300 is adjustable in accordance with the anatomical variation and distance between the nostrils. Right side of the slidable block 307 may have in-built screw threads or any other conventional means for aligning and securing the screw rod 315 coming from the lateral right edge of the horizontal bar and to allow to & fro movement of the slidable block 307, wherein the screw handle 317 is operably attached to the proximal end of the screw rod 315 outside the horizontal bar 300.

In another embodiment, the slidable block 307 and screw rod 315 placement may be on the left part of the horizontal bar 300, whereas hole 301 with smooth surrounding is on the right part of the horizontal bar 300.

In an exemplary embodiment, the circular holes 301, 309 on the horizontal bar 300 and the slidable block 307 are meant to affix the nasal cones 100 anteriorly and injection syringes 200 posteriorly.

In other exemplary embodiment, the slidable block 307 is adjustably fastened to a screw rod 315 by means of a bolt 319 or any other conventional means, and wherein the rod 315 is equipped with a screw handle 317 at its proximal end outside the horizontal bar 300, rotation of which moves the slidable block 307 within the rectangular slot 303 to adjust the hole 309 according to anatomical variation and distance of the nostrils.

According to present invention, the horizontal bar 300 is additionally equipped with a plurality of projections 321 at the dorsal surface, having a small round depression 323 at each of the proximal end. The round depression 323 is meant to receive and fix the extra-nasal mesh splint 400 for recording/imprinting impression of the extra-nasal surface.

In another embodiment of present invention, the horizontal bar 300 may be circular, rectangular, curved, oval shaped or as per the anatomical contour.

Figure 4:
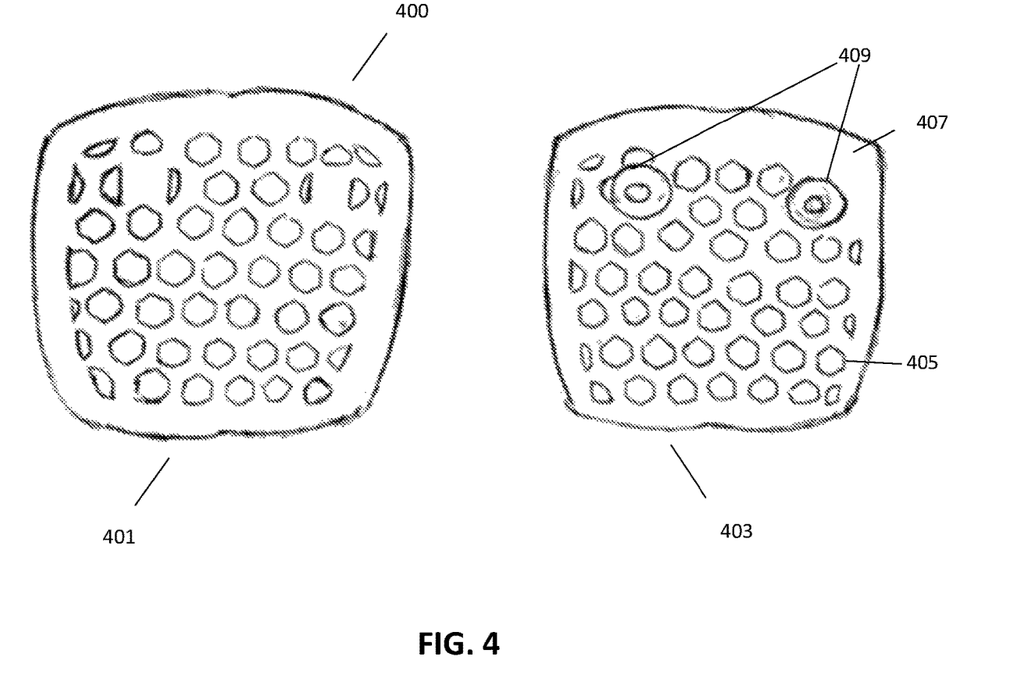
FIG. 4: Illustrates the extra-nasal mesh splint according to exemplary embodiment of the present invention.

FIG. 4 illustrates an extra-nasal mesh splint 400 according to embodiment of the present invention. Extra-nasal mesh splint 400 is trapezoid in shape with rounded edges, and has perforations 405 all over its surface except on its border edges 407. The ventral surface 403 of the splint contains two slots 409 projecting towards the nose for receiving and fixation of the rounded depressions 323 of the vertical projections 321 of the horizontal bar 300.

According to further embodiment of the present invention, the extra-nasal mesh splint 400 allows reliable connection of extra-nasal impression with intra-nasal impressions. It allows smooth removal of both extra and intra nasal impressions collectively and maintains the impressions in their natural anatomical relationship and provides support during model pouring.

Figure 5:
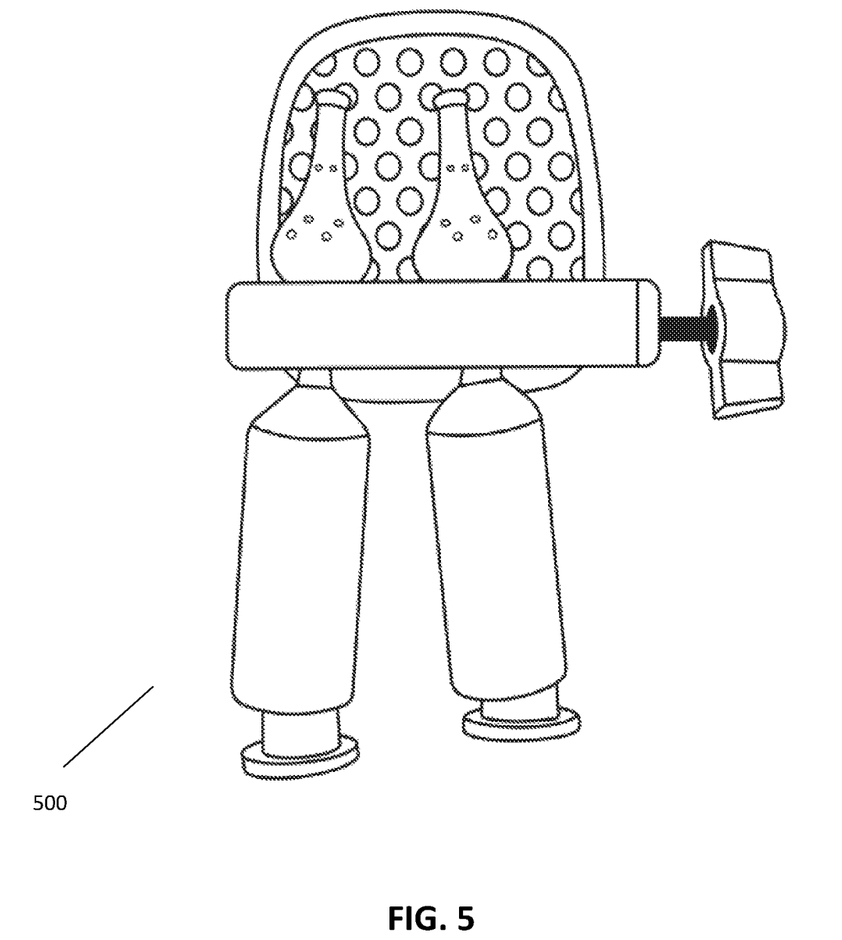
FIG. 5: Illustrates an assembled exemplary embodiment of the present invention.

FIG. 5 illustrates an assembled exemplary embodiment 500 of the present invention, wherein the detachable components are assembled in a nasal assembly.

In other embodiment of the present invention, the detachable components allow repetition of impression recording/imprinting in case of corrections.

In an exemplary embodiment as illustrated in FIG. 1-5, the horizontal bar 300 is a rectangular framework of 50 mm in width and 21 mm in height, comprising a hole 301 of 7 mm diameter on the left side and a rectangular slot 303 for receiving slidable block 307 on the right side. The slidable block 307 is 20 mm in width and 11 mm in height having a circular hole 309 in the center of around 7 mm diameter, for moving slidable block 307 inside the horizontal bar's rectangular slot 303 upon rotation of the screw rod 315. The length of screw rod 315 is 24 mm.

In another exemplary embodiment, the horizontal bar 300 comprises two vertical projections 321 with an inter-distance of 20 mm, wherein the length of each projection is 16 mm, thickness is 5 mm and there is a small depression 323 of 4 mm present at their tips for attachment of the extra-nasal mesh 400 to the assembly.

In further exemplary embodiment, the holes 301, 309 on the horizontal bar 300 are affixed with nasal cones 100 on the anterior surface and injection syringes 200 on the posterior surface. The nasal cones 100 are sorori shaped with mushroom shaped tip 101 and a base 107. The tip of the cone 101 is 5 mm in diameter without any perforation, whereas the base of cone 107 is 15 mm in diameter having perforation 105 of 1.5 mm in diameter all over its surface.

In another exemplary embodiment, the injection syringes 200 affixed at the posterior surface of the horizontal bar 300 comprises the patrix 203 and a matrix 201 portion, wherein the patrix 203 is a solid plunger of 36 mm in length and comprises a push handle 205 of diameter 18 mm at its distal end, whereas the matrix portion 201 having total length of 43 mm is a hollow cylinder of about 36 mm in length and 15 mm in diameter and has a capacity of 6361.73 mm$^3$.

In furthermore exemplary embodiment, the extra nasal mesh splint 400 comprises two slots 409 on the ventral side for receiving and fixation of the projections 321 coming out of the superior side of the horizontal bar, wherein the slots 409 have a diameter of 4 mm and are pointed 4 mm towards the nose. The thickness of extra nasal mesh splint 400 is 3 mm, width is 45 mm anteriorly and 55 mm posteriorly, and wherein the total length of the extra nasal mesh is 57 mm. The surface of extra-nasal mesh 400 has perforations 405 of 5 mm excluding the border 407 of the mesh which is around 4 mm.

In further embodiment, the anterior and medial provision of the injection syringes 200 allows it to be used for a single impression of nasal cavity or a collective impression of both nasal cavities whereas the vertical projections along with nasal cones 100 allow it to be used independently or in combination with the extra-nasal splint mesh 400.

According to embodiment of the present invention, the method of recording/imprinting the nasal impression involves placing the individual on a reclined seat at about 45° angle. The deeper part of the nasal cavity may be blocked as a precautionary measure in order to avoid entrapment of the material to flow into the posterior nasal cavity.

In further embodiment, the intra-nasal mucosal surface is covered with Vaseline, petroleum jelly or alike. Local anesthetic agent such as Xylocaine gel may optionally be applied to numb the intra-nasal surface and to prevent any painful experience. On the other hand, detachable components including the nasal cones 100 are joined to respective injection syringes 200 through the holes 301, 309 and assembled on the horizontal bar 300.

In another embodiment of the present invention, the impression material i.e. medium setting alginate material is mixed in a rubber bowl using spatula or auto-mixed using an alginate auto-mixer or a regular body silicone is mixed in an automixer syringe. The prepared material is then introduced in the injection syringes 200, following which, nasal cones 100 are affixed to the horizontal bar 300 and placed in each respective nostril to accommodate the proximity of nasal cavities and the impression material is slowly injected until the nasal cavity(ies) are completely filled. The material is allowed to set then washed under running water to remove the excessive secretions. The recorded/imprinted impression is then disinfected and filled sequentially with plaster of paris or any other material for model making.

According to another embodiment of the present invention, before insertion of the nasal cones 100 into the nasal cavity(ies), the individual/person may optionally be reclined further to 20° from the floor and soaked cotton gauze be placed on eyes of the individual as a precautionary measure. Then the impression material such as alginate/regular body silicone is poured over the entire extra-nasal surface, covering ala of the nose, nasal tips as well as its columella.

In further embodiment, impression plaster or quick setting plaster of paris is painted over the freshly poured alginate surface and immediately the extra-nasal mesh splint 400 is placed over the nose, whereas the slots 409 present on ventral surface of the extra-nasal mesh splint 400 is fixed to vertical projections 321 present on the horizontal bar 300.

In furthermore embodiment, as soon as the impression material sets, the whole nasal impression assembly 500 is removed in a postero medial direction. Remaining steps of removing excessive secretions and model making are carried out as per the method known per se.

According to the present invention, the impression material can be poured in separately or consecutively for taking the extra-nasal and intra-nasal impressions.

According to embodiment of the present invention, the nasal impression assembly 500 can be used for recording/imprinting a single intra-nasal impression or can be used as for recording combined impression of both the nasal cavities from extra-nasal as well as an intra-nasal surface.

Numerous characteristics and advantages have been set forth in the foregoing description, together with details of structure and function, it is intended that all matter contained interpreted as illustrative and not in a limiting sense. While the invention has been disclosed in several forms, it will be apparent to those skilled in the art that many modifications, additions, and deletions, especially in matters of shape, size, and arrangement of parts or components, can be made therein without departing from the spirit and scope of the invention and its equivalents as set forth in the following claims. Therefore, other modifications or embodiments as may be suggested by the teachings herein are particularly reserved as they fall within the breadth and scope of the claims here appended.

The invention claimed is:

1. A nasal impression assembly, comprising:
a detachable component including a horizontal bar,
a plurality of nasal cones, and
a pair of injection syringes;
wherein the pair of injection syringes and nasal cones are interconnected and removably coupled to anterior and posterior side of the horizontal bar through a plurality of circular holes; and
wherein at least one circular hole is positioned on a slidable block that is placed within a rectangular slot of the horizontal bar.

2. The nasal impression assembly of claim 1, wherein the horizontal bar has an additional small circular hole at its lateral edge.

3. The nasal impression assembly of claim 1, wherein the horizontal bar is additionally equipped with a plurality of projections on its dorsal surface.

4. The nasal impression assembly of claim 3, wherein an extra-nasal mesh splint is operably attached to the horizontal bar through the projections.

5. The nasal impression assembly of claim 2, wherein a screw rod passes across the small circular hole and wherein the screw rod is affixed with a screw handle at proximal end and the slidable block at its distal end.

6. The nasal impression assembly of claim 5, wherein the slidable block is moved forward and backward with rotation of the screw rod.

7. The nasal impression assembly of claim 1, wherein the slidable block is additionally equipped with an orifice having an inlet in its lateral edge.

8. The nasal impression assembly of claim 1, wherein the inlet in the orifice of the slidable block is coplanar with the small circular hole in the horizontal bar.

9. The nasal impression assembly of claim 1, wherein a screw rod is passed across the co-planar arrangement and fixed with the slidable block to control its movement.

10. The nasal impression assembly of claim 8, wherein the proximal end of the screw rod outside the orifice is secured with a screw handle, and wherein the distal end of the screw rod is secured with a bolt.

11. The nasal impression assembly of claim 1, wherein all the circular holes are internally lined with screw threads.

12. The nasal impression assembly of claim 1, wherein the nasal cone is sorori shaped with a mushroom shaped tip, a perforated base beneath the tip and screw threads at the extended protrusion of the base for affixation to the horizontal bar.

13. The nasal impression assembly of claim 1, wherein each injection syringe having a patrix part inside a matrix part;
wherein the matrix is a hollow cylinder having an axial cavity and screw threads etched at its hub; and
wherein the patrix part includes a plunger with a push handle at its distal end.

14. A method of imprinting/measuring the nasal impression using nasal assembly of claim 1, comprising the steps of:
filling the impression material in the syringe matrix;
introducing patrix part through axial cavity of the matrix;
affixing the injection syringes from the posterior side of the horizontal bar;
attaching the nasal cones from anterior side of the horizontal bar;
placing the nasal cones in the nostril after adjusting to the anatomical variation by moving the slidable block through rotation of the screw handle; pushing the patrix to introduce the impression material into the nasal cavity through the cones; and
recording the impression after the material is set for model making.

15. The method of imprinting/measuring the nasal impression of claim 14, wherein the nasal cones are mesially angulated to an angle of when attached to the horizontal bar.

16. The method of imprinting/measuring the nasal impression of claim 14, wherein the impression material is released into the nasal cavity from the perforations at base of the cone.

17. The method of imprinting/measuring the nasal impression of claim 14, wherein the tip of nasal cone is shaped to conform to the mesial tilt of the nasal cavities.

* * * * *